United States Patent [19]

Tomioka et al.

[11] Patent Number: 5,124,341
[45] Date of Patent: Jun. 23, 1992

[54] OXADIAZOLINONE DERIVATIVE AND ITS PRODUCTION AND USE

[75] Inventors: Hiroki Tomioka, Toyonaka; Noriyasu Sakamoto, Nishinomiya; Kimitoshi Umeda; Hiroaki Fujimoto, both of Toyonaka; Takao Ishiwatari, Minoo; Hirosi Kisida, Takarazuka, all of Japan

[73] Assignee: Sumitomo Chemical Company, Limited, Osaka, Japan

[21] Appl. No.: 629,706

[22] Filed: Dec. 18, 1990

[30] Foreign Application Priority Data

Dec. 25, 1989 [JP] Japan .................. 1-337697

[51] Int. Cl.$^5$ .............. C07D 271/113; A01N 43/82
[52] U.S. Cl. .................... 514/364; 514/340; 546/777; 548/144
[58] Field of Search .............. 548/144; 546/277; 514/364, 340

[56] References Cited

U.S. PATENT DOCUMENTS

| | | | |
|---|---|---|---|
| 3,385,862 | 5/1968 | Metivier et al. | 548/144 |
| 4,138,404 | 2/1979 | Fort | 548/144 |
| 4,943,583 | 7/1990 | Luthy | 548/144 |

FOREIGN PATENT DOCUMENTS

| | | |
|---|---|---|
| 0270061 | 6/1988 | European Pat. Off. . |
| 60-109578 | 6/1985 | Japan .................. 548/144 |
| 60-109578 | 6/1985 | Japan .................. 548/144 |
| 1081763 | 8/1967 | United Kingdom . |

Primary Examiner—Robert Gerstl
Attorney, Agent, or Firm—Stevens, Davis, Miller & Mosher

[57] ABSTRACT

The present invention relates to an oxadiazolinone derivative represented by the following general formula, a process for producing the same and insecticides containing the same as an active ingredient:

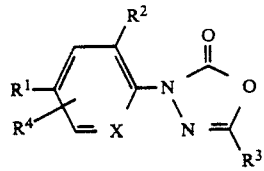

wherein $R^1$ is a haloalkyl group or a haloalkoxy group; $R^2$ is a halogen atom, nitro group, trifluoromethyl group of 1-pyrrolyl group; $R^3$ is a bicycloalkyl group, a methyl- or choro-substituted cycloalkyl group, an alkenyl group, a methyl-substituted cycloalkenyl group, 2-methyl-1,3-dithioran-2-yl group or an alkyl group, wherein the alkyl group may be substituted with a halogen atom, an alkoxy group, an alkylthio group, an alkylsulfinyl group, an alkylsulfonyl group or an alkoxycarbonyl group; $R^4$ is hydrogen atom or fluorine atom; and X is $CR^2$ or N.

The oxidiazolinone derivative can be used as an insecticide by formulating it into emulsifiable concentrates, wettable powders, dusts, granules, flowable concentrates and poison baits, etc..

10 Claims, No Drawings

OXADIAZOLINONE DERIVATIVE AND ITS PRODUCTION AND USE

The present invention relates to a novel oxadiazolinone derivative, a process for producing the same and insecticides containing the same as an active ingredient.

It is described in U.S. Pat. No. 3,385,862 that a certain oxadiazolinone derivative, for example, 5-tert-butyl-3-(2,4-dichlorophenyl)-1,3,4-oxadiazolin-2-one, is useful as an active ingredient of herbicide.

As a result of extensive investigations on compounds having an excellent insecticidal effect, the present inventors have found that an oxadiazolinone derivative shown by the general formula [I] described below exhibit an extremely high insecticidal effect and have accomplished the present invention.

That is, the present invention relates to the oxadiazolinone derivative represented by the general formula [I]:

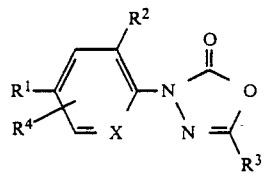

wherein $R^1$ is a haloalkyl group or a haloalkoxy group; $R^2$ is a halogen atom, nitro group, trifluoromethyl group or 1-pyrrolyl group; $R^3$ is a bicycloalkyl group, a methyl- or chloro-substituted cycloalkyl group, an alkenyl group, a methyl-substituted cycloalkenyl group, 2-methyl-1,3-dithioran-2-yl group or an alkyl group, wherein the alkyl group may be substituted with a halogen atom, an alkoxy group, an alkylthio group, an alkylsulfinyl group, an alkylsulfonyl group or an alkoxycarbonyl group; $R^4$ is hydrogen atom or fluorine atom; and X is $CR^2$ or N, (hereafter referred to as the compound(s) of the present invention), processes for production thereof, insecticidal compositions comprising the same as active ingredient, and a method for controlling insect pests using the same.

In general formula [I], the alkyl group in the haloalkyl group or the alkoxy group in the haloalkoxy group shown by $R^1$ refers to a group having 1 to 3 carbon atoms, preferably methyl and methoxy. Examples of the halogen as the substituent include fluorine atom, chlorine atom or bromine atom, preferably fluorine atom. The most preferred example of $R^1$ is trifluoromethyl. Examples of the halogen atom shown by $R^2$ include fluorine atom, chlorine atom or bromine stom, preferably fluorine atom and chlorine atom. As $R^2$, a halogen atom and nitro group are preferred. Examples of the alicyclic group shown by $R^3$ are a group of 3- to 6-membered ring. The aliphatic group may be exemplified by a group having 1 to 5 carbon atoms except for the substituent, preferably a group having 2 to 5 carbon atoms. Specific examples of $R^3$ which are preferred are an alkyl group having 2 to 5 carbon atoms and the halogen atom as a substituent on the alkyl group is exemplified by fluorine atom, chlorine atom and bromine atom. Further the alkoxy group, alkylthio group, alkylsulfinyl group, alkylsulfonyl group or alkoxycarbonyl group also used as the substituent is exemplified by those having 1 to 3 carbon atoms. Of these substituents, the halogen atom, alkoxy group, alkylthio group, alkylsulfinyl group and alkylsulfonyl group are preferred. More preferred examples are an alkoxy group having 1 to 2 carbon atoms, an alkylthio group having 1 to 2 carbon atoms, an alkylsulfinyl group and alkylsulfonyl group having 1 to 2 carbon atoms. Among them, methylthio group is a most preferred substituent.

The compounds of the present invention can be produced according to the following reaction scheme (Reaction scheme 1).

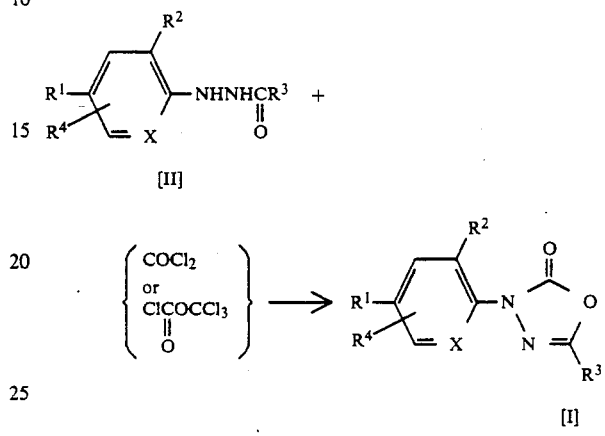

wherein $R^1$, $R^2$, $R^3$, $R^4$ and X have the same significances as above.

The compounds of the present invention can be produced by reacting hydrazides [II] with phosgene or trichloromethyl chloroformate at about $-5°$ C. to about $150°$ C. for about 1 to about 24 hours in a solvent in the presence or absence of an reagent for removing a hydrogen halide.

The compounds of the present invention may also be produced according to the following reaction scheme (Reaction scheme 2).

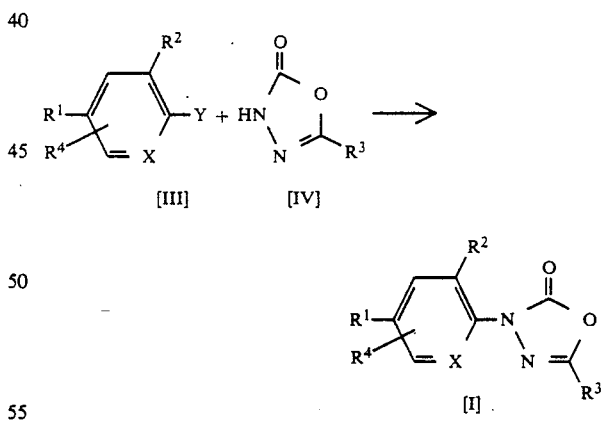

wherein $R^1$, $R^2$, $R^3$, $R^4$ and X have the same significances as above; and Y is a halogen atom.

The compounds of the present invention can be produced by reacting halide compounds [III] with oxadiazolinone derivatives [IV] at about $0°$ C. to about $150°$ C. for about 1 to about 24 hours in a solvent in the presence of an reagent for removing a hydrogen halide.

Amounts of the reactants provided for the reactions are described below. In (Reaction scheme 1), 1 to 9 molar equivalents of phosgene or trichloromethyl chloroformate and 0 to 7 molar equivalents of the reagent for removing a hydrogen halide are used per mole of the hydrazide represented by the general formula [II]. In (Reaction scheme 2), 0.5 to 2 molar equivalents of the oxadiazolinone derivatives represented by the general formula [IV] and 1 to 4 molar equivalents of the reagent for removing a hydrogen halide are used per mole of the halide compounds represented by the general formula [III].

Examples of the solvent which is used for the both reactions described above include aliphatic hydrocarbons such as hexane, heptane, ligroin, petroleum ether, etc.; aromatic hydrocarbons such as benzene, toluene, xylene, etc.; halogenated hydrocarbons such as chloroform, carbon tetrachloride, dichloroethane, chlorobenzene, dichlorobenzene, etc.; ethers such as diethyl ether, diisopropyl ether, dioxan, tetrahydrofuran, ethylene glycol dimethyl ether, etc.; ketones such as acetone, methyl ethyl ketone, methyl isobutyl ketone, isophorone, cyclohexanone, etc.; esters such as ethyl acetate, butyl acetate, etc.; nitro compounds such as nitroethane, nitrobenzene, etc.; nitriles such as acetonitrile, isobutyronitrile, etc.; tertiary amines such as pyridine, triethylamine, N,N-diethylaniline, tributylamine, N-methylmorpholine, etc.; acid amides such as formamide, N,N-dimethylformamide, N,N-dimethylacetamide, etc.; sulfur compounds such as dimethylsulfoxide, sulfolane, etc.; or mixtures thereof.

Examples of the reagent of removing hydrogen halide include organic bases such as pyridine, triethylamine, N,N-diethylaniline, etc.; inorganic bases such as sodium hydride, sodium carbonate, potassium carbonate, etc.

After completion of the reaction, post-treatment follows in a conventional manner. If necessary and desired, the product may further be purified by chromatography, distillation, recrystallization, etc.

The hydrazide derivatives represented by the general formula [II], the oxadiazolinone derivatives represented by the general formula [IV] and the halide compounds represented by the general formula [III] which are used as raw materials for the compounds of the present invention are prepared by the methods described in J. March, "Advanced Organic Chemistry", second edition, page 386; Chem. Ber., 82, 121 (1949); and West German Patent 2,311,638, European Patent 23,100, Belgian Patent 865,137 and J. Org. Chem., 25, 1710 (1960), British Patent 1,121,211 respectively, or in a manner similar to the methods. Furthermore, the compounds represented by the general formula [V]:

[V]

$$R^1-\underset{R^4}{\overset{R^2}{\diagdown}}\text{—NHNH}_2$$

wherein $R^1$, $R^2$, $R^4$ and X have the same significances as above; which can be raw materials of the hydrazide derivatives represented by the general formula [II] may be produced by the methods described in, for example, U.S. Pat. No. 4,127,575, U.S. Pat. No. 3,609,158, DE-OS 2,558,399, and J. Chem. Soc., C. 1971, 167–174.

Examples of the compounds of the present invention are shown in Tables 1-1 and 1-2 below.

TABLE 1-1

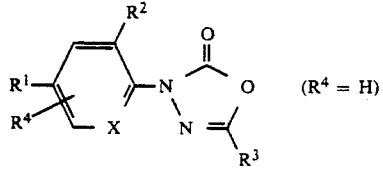

($R^4$ = H)

| $R^1$ | $R^2$ | $R^3$ | X |
|---|---|---|---|
| $CF_3$ | Cl | -tert-$C_4H_9$ | CCl |
| $CF_3$ | Cl | —$C(CH_3)_2SCH_3$ | CCl |
| $CF_3$ | Cl | —$CF_2CF_3$ | CCl |
| $CF_3$ | Cl | —CH(CH$_3$)(CF$_3$) | CCl |
| $CF_3$ | Cl | -iso$C_3H_7$ | CCl |
| $CF_3$ | Cl | —$C(CH_3)=CH_2$ | CCl |
| $CF_3$ | Cl | —$CF_2CF_2CF_3$ | CCl |
| $CF_3$ | Cl | —$C(CH_3)_2CH_2Cl$ | CCl |
| $CF_3$ | Cl | —$C(CH_3)_2OCH_3$ | CCl |
| $CF_3$ | Cl | —$C(CF_3)_2CH_3$ | CCl |
| $CF_3$ | Cl | —$C(CH_3)_2COOC_2H_5$ | CCl |
| $CF_3$ | Cl | -sec-$C_4H_9$ | CCl |
| $CF_3$ | Cl | 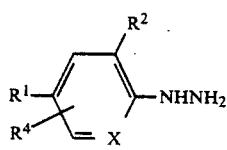 (1-methylcyclopropyl) | CCl |
| $CF_3$ | Cl | (dithiolane with CH$_3$, CH$_3$) | CCl |
| $CF_3$ | Cl | —$C(CH_3)_2SO_2CH_3$ | CCl |
| $CF_3$ | Cl | —$C(CH_3)_2SC_2H_5$ | CCl |
| $CF_3$ | Cl | —$C(CH_3)_2$S-n-$C_3H_7$ | CCl |
| $CF_3$ | Cl | —$C(CH_3)_2SO_2C_2H_5$ | CCl |
| $CF_3$ | Cl | —$C(CH_3)_2SO_2$-n-$C_3H_7$ | CCl |
| $CF_3$ | Cl | —$C_2H_5$ | CCl |
| $CF_3$ | Cl | —$C(CH_3)_2C_2H_5$ | CCl |
| $CF_3$ | Cl | (1-methyl-2-chlorocyclopropyl) | CCl |
| $CF_3$ | Cl | (1-methylcyclohexyl) | CCl |
| $CF_3$ | Cl | (1-methylcyclopentyl) | CCl |
| $CF_3$ | Cl | -n-$C_3H_7$ | CCl |
| $CF_3$ | Cl | —CH($C_2H_5$)$_2$ | CCl |
| $CF_3$ | $NO_2$ | -tert-$C_4H_9$ | $CNO_2$ |
| $CF_3$ | $NO_2$ | —$C(CH_3)_2SCH_3$ | $CNO_2$ |
| $CF_3$ | $NO_2$ | —$CF_2CF_3$ | $CNO_2$ |

TABLE 1-1-continued

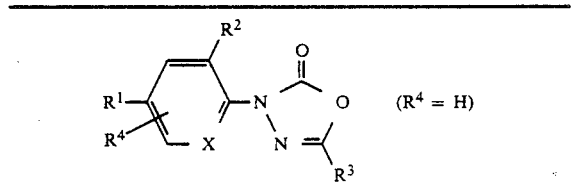

($R^4$ = H)

| $R^1$ | $R^2$ | $R^3$ | X |
|---|---|---|---|
| $CF_3$ | $NO_2$ | $-CH(CH_3)(CF_3)$ | $CNO_2$ |
| $CF_3$ | $NO_2$ | -iso$C_3H_7$ | $CNO_2$ |
| $CF_3$ | $NO_2$ | $-C(CH_3)=CH_2$ | $CNO_2$ |
| $CF_3$ | $NO_2$ | $-CF_2CF_2CF_3$ | $CNO_2$ |
| $CF_3$ | $NO_2$ | $-C(CH_3)_2CH_2Cl$ | $CNO_2$ |
| $CF_3$ | $NO_2$ | $-C(CH_3)_2OCH_3$ | $CNO_2$ |
| $CF_3$ | $NO_2$ | $-C(CF_3)_2CH_3$ | $CNO_2$ |
| $CF_3$ | $NO_2$ | $-C(CH_3)_2COOC_2H_5$ | $CNO_2$ |
| $CF_3$ | $NO_2$ | -sec-$C_4H_9$ | $CNO_2$ |
| $CF_3$ | $NO_2$ | 1-methylcyclopropyl | $CNO_2$ |
| $CF_3$ | $NO_2$ | 2-methyl-1,3-dithiolanyl | $CNO_2$ |
| $CF_3$ | $NO_2$ | $-C(CH_3)_2SO_2CH_3$ | $CNO_2$ |
| $CF_3$ | $NO_2$ | $-C(CH_3)_2SC_2H_5$ | $CNO_2$ |
| $CF_3$ | $NO_2$ | $-C(CH_3)_2S$-n-$C_3H_7$ | $CNO_2$ |
| $CF_3$ | $NO_2$ | $-C(CH_3)_2SO_2C_2H_5$ | $CNO_2$ |
| $CF_3$ | $NO_2$ | $-C(CH_3)_2SO_2$-n-$C_3H_7$ | $CNO_2$ |
| $CF_3$ | $NO_2$ | $-C_2H_5$ | $CNO_2$ |
| $CF_3$ | $NO_2$ | $-C(CH_3)_2C_2H_5$ | $CNO_2$ |
| $CF_3$ | $NO_2$ | 1-methyl-2,2-dichlorocyclopropyl | $CNO_2$ |
| $CF_3$ | $NO_2$ | 1-methylcyclohexyl | $CNO_2$ |
| $CF_3$ | $NO_2$ | 1-methylcyclopentyl | $CNO_2$ |
| $CF_3$ | $NO_2$ | -n-$C_3H_7$ | $CNO_2$ |
| $CF_3$ | $NO_2$ | $-CH(C_2H_5)_2$ | $CNO_2$ |
| $CF_3$ | Cl | -tert-$C_4H_9$ | $CNO_2$ |
| $CF_3$ | Cl | $-C(CH_3)_2SCH_3$ | $CNO_2$ |
| $CF_3$ | Cl | $-CF_2CF_3$ | $CNO_2$ |
| $CF_3$ | Cl | $-CH(CH_3)(CF_3)$ | $CNO_2$ |
| $CF_3$ | Cl | -iso$C_3H_7$ | $CNO_2$ |
| $CF_3$ | Cl | $-C(CH_3)=CH_2$ | $CNO_2$ |
| $CF_3$ | Cl | $-CF_2CF_2CF_3$ | $CNO_2$ |
| $CF_3$ | Cl | $-C(CH_3)_2CH_2Cl$ | $CNO_2$ |
| $CF_3$ | Cl | $-C(CH_3)_2OCH_3$ | $CNO_2$ |
| $CF_3$ | Cl | $-C(CF_3)_2CH_3$ | $CNO_2$ |
| $CF_3$ | Cl | $-C(CH_3)_2COOC_2H_5$ | $CNO_2$ |
| $CF_3$ | Cl | -sec-$C_4H_9$ | $CNO_2$ |
| $CF_3$ | Cl | 1-methylcyclopropyl | $CNO_2$ |
| $CF_3$ | Cl | 2-methyl-1,3-dithiolanyl | $CNO_2$ |
| $CF_3$ | Cl | $-C(CH_3)_2SO_2CH_3$ | $CNO_2$ |
| $CF_3$ | Cl | $-C(CH_3)_2SC_2H_5$ | $CNO_2$ |
| $CF_3$ | Cl | $-C(CH_3)_2S$-n-$C_3H_7$ | $CNO_2$ |
| $CF_3$ | Cl | $-C(CH_3)_2SO_2C_2H_5$ | $CNO_2$ |
| $CF_3$ | Cl | $-C(CH_3)_2SO_2$-n-$C_3H_7$ | $CNO_2$ |
| $CF_3$ | Cl | $-C_2H_5$ | $CNO_2$ |
| $CF_3$ | Cl | $-C(CH_3)_2C_2H_5$ | $CNO_2$ |
| $CF_3$ | Cl | 1-methyl-2,2-dichlorocyclopropyl | $CNO_2$ |
| $CF_3$ | Cl | 1-methylcyclohexyl | $CNO_2$ |
| $CF_3$ | Cl | 1-methylcyclopentyl | $CNO_2$ |
| $CF_3$ | Cl | -n-$C_3H_7$ | $CNO_2$ |
| $CF_3$ | Cl | $-CH(C_2H_5)_2$ | $CNO_2$ |
| $CF_3$ | Cl | -tert-$C_4H_9$ | CF |
| $CF_3$ | Cl | $-C(CH_3)_2SCH_3$ | CF |
| $CF_3$ | Cl | $-CF_2CF_3$ | CF |
| $CF_3$ | Cl | $-CH(CH_3)(CF_3)$ | CF |
| $CF_3$ | Cl | -iso$C_3H_7$ | CF |
| $CF_3$ | Cl | $-C(CH_3)=CH_2$ | CF |
| $CF_3$ | Cl | $-CF_2CF_2CF_3$ | CF |
| $CF_3$ | Cl | $-C(CH_3)_2CH_2Cl$ | CF |
| $CF_3$ | Cl | $-C(CH_3)_2OCH_3$ | CF |
| $CF_3$ | Cl | $-C(CF_3)_2CH_3$ | CF |
| $CF_3$ | Cl | $-C(CH_3)_2COOC_2H_5$ | CF |

TABLE 1-1-continued

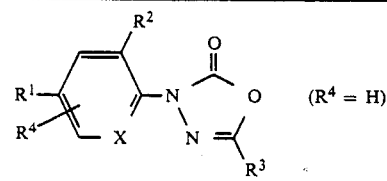

($R^4 = H$)

| $R^1$ | $R^2$ | $R^3$ | X |
|---|---|---|---|
| $CF_3$ | Cl | -sec-$C_4H_9$ | CF |
| $CF_3$ | Cl | cyclopropyl-$CH_3$ | CF |
| $CF_3$ | Cl | 1,3-dithiolane-2-yl with $CH_3$ | CF |
| $CF_3$ | Cl | $-C(CH_3)_2SO_2CH_3$ | CF |
| $CF_3$ | Cl | $-C(CH_3)_2SC_2H_5$ | CF |
| $CF_3$ | Cl | $-C(CH_3)_2S$-n-$C_3H_7$ | CF |
| $CF_3$ | Cl | $-C(CH_3)_2SO_2C_2H_5$ | CF |
| $CF_3$ | Cl | $-C(CH_3)_2SO_2$-n-$C_3H_7$ | CF |
| $CF_3$ | Cl | $-C_2H_5$ | CF |
| $CF_3$ | Cl | $-C(CH_3)_2C_2H_5$ | CF |
| $CF_3$ | Cl | 1,1-dichlorocyclopropyl-2-$CH_3$ | CF |
| $CF_3$ | Cl | 1-methylcyclohexyl | CF |
| $CF_3$ | Cl | 1-methylcyclopentyl | CF |
| $CF_3$ | Cl | -n-$C_3H_7$ | CF |
| $CF_3$ | Cl | $-CH(C_2H_5)_2$ | CF |
| $CF_3$ | Cl | -tert-$C_4H_9$ | N |
| $CF_3$ | Cl | $-C(CH_3)_2SCH_3$ | N |
| $CF_3$ | Cl | $-CF_2CF_3$ | N |
| $CF_3$ | Cl | $-CH(CH_3)CF_3$ | N |
| $CF_3$ | Cl | -iso$C_3H_7$ | N |
| $CF_3$ | Cl | $-C(CH_3)=CH_2$ | N |
| $CF_3$ | Cl | $-CF_2CF_2CF_3$ | N |
| $CF_3$ | Cl | $-C(CH_3)_2CH_2Cl$ | N |
| $CF_3$ | Cl | $-C(CH_3)_2OCH_3$ | N |
| $CF_3$ | Cl | $-C(CF_3)_2CH_3$ | N |
| $CF_3$ | Cl | $-C(CH_3)_2COOC_2H_5$ | N |
| $CF_3$ | Cl | -sec-$C_4H_9$ | N |
| $CF_3$ | Cl | cyclopropyl-$CH_3$ | N |

TABLE 1-1-continued

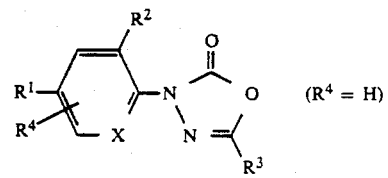

($R^4 = H$)

| $R^1$ | $R^2$ | $R^3$ | X |
|---|---|---|---|
| $CF_3$ | Cl | 1,3-dithiolane-2-yl with $CH_3$ | N |
| $CF_3$ | Cl | $-C(CH_3)_2SO_2CH_3$ | N |
| $CF_3$ | Cl | $-C(CH_3)_2SC_2H_5$ | N |
| $CF_3$ | Cl | $-C(CH_3)_2S$-n-$C_3H_7$ | N |
| $CF_3$ | Cl | $-C(CH_3)_2SO_2C_2H_5$ | N |
| $CF_3$ | Cl | $-C(CH_3)_2SO_2$-n-$C_3H_7$ | N |
| $CF_3$ | Cl | $-C_2H_5$ | N |
| $CF_3$ | Cl | $-C(CH_3)_2C_2H_5$ | N |
| $CF_3$ | Cl | 1,1-dichlorocyclopropyl-2-$CH_3$ | N |
| $CF_3$ | Cl | 1-methylcyclohexyl | N |
| $CF_3$ | Cl | 1-methylcyclopentyl | N |
| $CF_3$ | Cl | -n-$C_3H_7$ | N |
| $CF_3$ | Cl | $-CH(C_2H_5)_2$ | N |
| $CF_3$ | F | -tert-$C_4H_9$ | CF |
| $CF_3$ | F | $-C(CH_3)_2SCH_3$ | CF |
| $CF_3$ | F | $-CF_2CF_3$ | CF |
| $CF_3$ | F | $-CH(CH_3)CF_3$ | CF |
| $CF_3$ | F | -iso$C_3H_7$ | CF |
| $CF_3$ | F | $-C(CH_3)=CH_2$ | CF |
| $CF_3$ | F | $-CF_2CF_2CF_3$ | CF |
| $CF_3$ | F | $-C(CH_3)_2CH_2Cl$ | CF |
| $CF_3$ | F | $-C(CH_3)_2OCH_3$ | CF |
| $CF_3$ | F | $-C(CF_3)_2CH_3$ | CF |
| $CF_3$ | F | $-C(CH_3)_2COOC_2H_5$ | CF |
| $CF_3$ | F | -sec-$C_4H_9$ | CF |
| $CF_3$ | F | cyclopropyl-$CH_3$ | CF |
| $CF_3$ | F | 1,3-dithiolane-2-yl with $CH_3$ | CF |

TABLE 1-1-continued

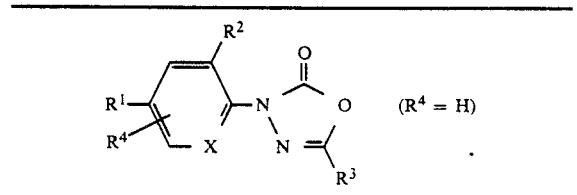

(R⁴ = H)

| R¹ | R² | R³ | X |
|---|---|---|---|
| CF₃ | F | —C(CH₃)₂SO₂CH₃ | CF |
| CF₃ | F | —C(CH₃)₂SC₂H₅ | CF |
| CF₃ | F | —C(CH₃)₂S-n-C₃H₇ | CF |
| CF₃ | F | —C(CH₃)₂SO₂C₂H₅ | CF |
| CF₃ | F | —C(CH₃)₂SO₂-n-C₃H₇ | CF |
| CF₃ | F | —C₂H₅ | CF |
| CF₃ | F | —C(CH₃)₂C₂H₅ | CF |
| CF₃ | F | 1,1-dichloro-2-methylcyclopropyl | CF |
| CF₃ | F | 1-methylcyclohexyl | CF |
| CF₃ | F | 1-methylcyclopentyl | CF |
| CF₃ | F | -n-C₃H₇ | CF |
| CF₃ | F | —CH(C₂H₅)₂ | CF |
| CF₃ | -N-pyrrolyl | -tert-C₄H₉ | CCl |
| CF₃ | -N-pyrrolyl | —C(CH₃)₂SCH₃ | CCl |
| CF₃ | -N-pyrrolyl | —CF₂CF₃ | CCl |
| CF₃ | -N-pyrrolyl | —CH(CH₃)(CF₃) | CCl |
| CF₃ | -N-pyrrolyl | -isoC₃H₇ | CCl |
| CF₃ | -N-pyrrolyl | —C(CH₃)=CH₂ | CCl |
| CF₃ | -N-pyrrolyl | —CF₂CF₂CF₃ | CCl |
| CF₃ | -N-pyrrolyl | —C(CH₃)₂CH₂Cl | CCl |
| CF₃ | -N-pyrrolyl | —C(CH₃)₂OCH₃ | CCl |
| CF₃ | -N-pyrrolyl | —C(CF₃)₂CH₃ | CCl |
| CF₃ | -N-pyrrolyl | —C(CH₃)₂COOC₂H₅ | CCl |
| CF₃ | -N-pyrrolyl | -sec-C₄H₉ | CCl |
| CF₃ | -N-pyrrolyl | 1-methylcyclopropyl | CCl |
| CF₃ | -N-pyrrolyl | 2-methyl-1,3-dithiolan-2-yl | CCl |
| CF₃ | -N-pyrrolyl | —C(CH₃)₂SO₂CH₃ | CCl |
| CF₃ | -N-pyrrolyl | —C(CH₃)₂SC₂H₅ | CCl |
| CF₃ | -N-pyrrolyl | —C(CH₃)₂S-n-C₃H₇ | CCl |

TABLE 1-1-continued (R⁴ = H) structure with R¹, R², R³, R⁴, X substituents on the hydrazone/oxazoline scaffold.

| R¹ | R² | R³ | X |
|---|---|---|---|
| CF₃ | —N-pyrrolyl | —C(CH₃)₂SO₂C₂H₅ | CCl |
| CF₃ | —N-pyrrolyl | —C(CH₃)₂SO₂-n-C₃H₇ | CCl |
| CF₃ | —N-pyrrolyl | —C₂H₅ | CCl |
| CF₃ | —N-pyrrolyl | —C(CH₃)₂C₂H₅ | CCl |
| CF₃ | —N-pyrrolyl | 1,1-dichloro-2-methylcyclopropyl | CCl |
| CF₃ | —N-pyrrolyl | 1-methylcyclohexyl | CCl |
| CF₃ | —N-pyrrolyl | 1-methylcyclopentyl | CCl |
| CF₃ | —N-pyrrolyl | -n-C₃H₇ | CCl |
| CF₃ | —N-pyrrolyl | —CH(C₂H₅)₂ | CCl |
| OCF₃ | —N-pyrrolyl | -tert-C₄H₉ | CCl |
| OCF₃ | —N-pyrrolyl | —C(CH₃)₂SCH₃ | CCl |
| OCF₃ | Cl | —CF₂CF₃ | CCl |
| OCF₃ | Cl | —CH(CH₃)CF₃ | CCl |
| OCF₃ | Cl | -isoC₃H₇ | CCl |
| OCF₃ | Cl | —C(CH₃)=CH₂ | CCl |
| OCF₃ | Cl | —CF₂CF₂CF₃ | CCl |
| OCF₃ | Cl | —C(CH₃)₂CH₂Cl | CCl |
| OCF₃ | Cl | —C(CH₃)₂OCH₃ | CCl |
| OCF₃ | Cl | —C(CF₃)₂CH₃ | CCl |
| OCF₃ | Cl | —C(CH₃)₂COOC₂H₅ | CCl |
| OCF₃ | Cl | -sec-C₄H₉ | CCl |
| OCF₃ | Cl | 1-methylcyclopropyl | CCl |
| OCF₃ | Cl | 2-methyl-1,3-dithiolan-2-yl | CCl |
| OCF₃ | Cl | —C(CH₃)₂SO₂CH₃ | CCl |
| OCF₃ | Cl | —C(CH₃)₂SC₂H₅ | CCl |
| OCF₃ | Cl | —C(CH₃)₂S-n-C₃H₇ | CCl |
| OCF₃ | Cl | —C(CH₃)₂SO₂C₂H₅ | CCl |
| OCF₃ | Cl | —C(CH₃)₂SO₂-n-C₃H₇ | CCl |
| OCF₃ | Cl | —C₂H₅ | CCl |
| OCF₃ | Cl | —C(CH₃)₂C₂H₅ | CCl |
| OCF₃ | Cl | 1,1-dichloro-2-methylcyclopropyl | CCl |
| OCF₃ | Cl | 1-methylcyclohexyl | CCl |
| OCF₃ | Cl | 1-methylcyclopentyl | CCl |
| OCF₃ | Cl | -n-C₃H₇ | CCl |
| OCF₃ | Cl | —CH(C₂H₅)₂ | CCl |
| CF₃ | Cl | —C(CH₃)₂COOCH₃ | CCl |
| CF₃ | Cl | —C(CH₃)₂COOCH₃ | CNO₂ |
| CF₃ | Cl | —C(CH₃)₂COOCH₃ | CF |
| CF₃ | Cl | —C(CH₃)₂COOCH₃ | N |
| CF₃ | NO₂ | —C(CH₃)₂COOCH₃ | CNO₂ |
| CF₃ | F | —C(CH₃)₂COOCH₃ | CF |

TABLE 1-1-continued ($R^4 = H$)

| $R^1$ | $R^2$ | $R^3$ | X |
|---|---|---|---|
| CF$_3$ | —N(pyrrole) | —C(CH$_3$)$_2$COOCH$_3$ | CCl |
| OCF$_3$ | Cl | —C(CH$_3$)$_2$COOCH$_3$ | CCl |
| CF$_3$ | Cl | —C(CH$_3$)$_2$S-isoC$_3$H$_7$ | CCl |
| CF$_3$ | Cl | —C(CH$_3$)$_2$S-isoC$_3$H$_7$ | CNO$_2$ |
| CF$_3$ | Cl | —C(CH$_3$)$_2$S-isoC$_3$H$_7$ | CF |
| CF$_3$ | Cl | —C(CH$_3$)$_2$S-isoC$_3$H$_7$ | N |
| CF$_3$ | NO$_2$ | —C(CH$_3$)$_2$S-isoC$_3$H$_7$ | CNO$_2$ |
| CF$_3$ | F | —C(CH$_3$)$_2$S-isoC$_3$H$_7$ | CF |
| CF$_3$ | —N(pyrrole) | —C(CH$_3$)$_2$S-isoC$_3$H$_7$ | CCl |
| OCF$_3$ | Cl | —C(CH$_3$)$_2$S-isoC$_3$H$_7$ | CCl |
| CF$_3$ | Cl | —C(CH$_3$)$_2$S-sec-C$_4$H$_9$ | CCl |
| CF$_3$ | Cl | —C(CH$_3$)$_2$S-sec-C$_4$H$_9$ | CNO$_2$ |
| CF$_3$ | Cl | —C(CH$_3$)$_2$S-sec-C$_4$H$_9$ | CF |
| CF$_3$ | Cl | —C(CH$_3$)$_2$S-sec-C$_4$H$_9$ | N |
| CF$_3$ | NO$_2$ | —C(CH$_3$)$_2$S-sec-C$_4$H$_9$ | CNO$_2$ |
| CF$_3$ | F | —C(CH$_3$)$_2$S-sec-C$_4$H$_9$ | F |
| CF$_3$ | —N(pyrrole) | —C(CH$_3$)$_2$S-sec-C$_4$H$_9$ | CCl |
| OCF$_3$ | Cl | —C(CH$_3$)$_2$S-sec-C$_4$H$_9$ | CCl |
| CF$_3$ | Cl | —C(CH$_3$)$_2$S-isoC$_4$H$_9$ | CCl |
| CF$_3$ | Cl | —C(CH$_3$)$_2$S-isoC$_4$H$_9$ | CNO$_2$ |
| CF$_3$ | Cl | —C(CH$_3$)$_2$S-isoC$_4$H$_9$ | CF |
| CF$_3$ | Cl | —C(CH$_3$)$_2$S-isoC$_4$H$_9$ | N |
| CF$_3$ | NO$_2$ | —C(CH$_3$)$_2$S-isoC$_4$H$_9$ | CNO$_2$ |
| CF$_3$ | F | —C(CH$_3$)$_2$S-isoC$_4$H$_9$ | CF |
| CF$_3$ | —N(pyrrole) | —C(CH$_3$)$_2$S-isoC$_4$H$_9$ | CCl |
| OCF$_3$ | Cl | —C(CH$_3$)$_2$S-isoC$_4$H$_9$ | CCl |
| CF$_3$ | Cl | —C(CH$_3$)$_2$S-tert-C$_4$H$_9$ | CCl |
| CF$_3$ | Cl | —C(CH$_3$)$_2$S-tert-C$_4$H$_9$ | CNO$_2$ |
| CF$_3$ | Cl | —C(CH$_3$)$_2$S-tert-C$_4$H$_9$ | CF |
| CF$_3$ | Cl | —C(CH$_3$)$_2$S-tert-C$_4$H$_9$ | N |
| CF$_3$ | NO$_2$ | —C(CH$_3$)$_2$S-tert-C$_4$H$_9$ | CNO$_2$ |
| CF$_3$ | F | —C(CH$_3$)$_2$S-tert-C$_4$H$_9$ | CF |
| CF$_3$ | —N(pyrrole) | —C(CH$_3$)$_2$S-tert-C$_4$H$_9$ | CCl |
| OCF$_3$ | Cl | —C(CH$_3$)$_2$S-tert-C$_4$H$_9$ | CCl |
| CF$_3$ | Cl | —C(C$_2$H$_5$)$_2$CH$_3$ | CCl |
| CF$_3$ | Cl | —C(C$_2$H$_5$)$_2$CH$_3$ | CNO$_2$ |
| CF$_3$ | Cl | —C(C$_2$H$_5$)$_2$CH$_3$ | CF |
| CF$_3$ | Cl | —C(C$_2$H$_5$)$_2$CH$_3$ | N |
| CF$_3$ | NO$_2$ | —C(C$_2$H$_5$)$_2$CH$_3$ | CNO$_2$ |
| CF$_3$ | F | —C(C$_2$H$_5$)$_2$CH$_3$ | CF |
| CF$_3$ | —N(pyrrole) | —C(C$_2$H$_5$)$_2$CH$_3$ | CCl |
| OCF$_3$ | Cl | —C(C$_2$H$_5$)$_2$CH$_3$ | CCl |
| CF$_3$ | Cl | —C(CH$_3$)$_2$OC$_2$H$_5$ | CCl |
| CF$_3$ | Cl | —C(CH$_3$)$_2$OC$_2$H$_5$ | CNO$_2$ |
| CF$_3$ | Cl | —C(CH$_3$)$_2$OC$_2$H$_5$ | CF |
| CF$_3$ | Cl | —C(CH$_3$)$_2$OC$_2$H$_5$ | N |
| CF$_3$ | NO$_2$ | —C(CH$_3$)$_2$OC$_2$H$_5$ | CNO$_2$ |
| CF$_3$ | F | —C(CH$_3$)$_2$OC$_2$H$_5$ | CF |
| CF$_3$ | —N(pyrrole) | —C(CH$_3$)$_2$OC$_2$H$_5$ | CCl |
| OCF$_3$ | Cl | —C(CH$_3$)$_2$OC$_2$H$_5$ | CCl |
| CF$_3$ | Cl | —C(CH$_3$)$_2$O-n-C$_3$H$_7$ | CCl |
| CF$_3$ | Cl | —C(CH$_3$)$_2$O-n-C$_3$H$_7$ | CNO$_2$ |
| CF$_3$ | Cl | —C(CH$_3$)$_2$O-n-C$_3$H$_7$ | CF |
| CF$_3$ | Cl | —C(CH$_3$)$_2$O-n-C$_3$H$_7$ | N |
| CF$_3$ | NO$_2$ | —C(CH$_3$)$_2$O-n-C$_3$H$_7$ | CNO$_2$ |
| CF$_3$ | F | —C(CH$_3$)$_2$O-n-C$_3$H$_7$ | CF |
| CF$_3$ | —N(pyrrole) | —C(CH$_3$)$_2$O-n-C$_3$H$_7$ | CCl |
| OCF$_3$ | Cl | —C(CH$_3$)$_2$O-n-C$_3$H$_7$ | CCl |
| CF$_3$ | Cl | —CH$_2$OCH$_3$ | CCl |
| CF$_3$ | Cl | —CH$_2$OCH$_3$ | CNO$_2$ |
| CF$_3$ | Cl | —CH$_2$OCH$_3$ | CF |
| CF$_3$ | Cl | —CH$_2$OCH$_3$ | N |
| CF$_3$ | NO$_2$ | —CH$_2$OCH$_3$ | CNO$_2$ |
| CF$_3$ | F | —CH$_2$OCH$_3$ | CF |
| CF$_3$ | —N(pyrrole) | —CH$_2$OCH$_3$ | CCl |
| OCF$_3$ | Cl | —CH$_2$OCH$_3$ | CCl |
| CF$_3$ | Cl | —C(CH$_3$)$_2$O-sec-C$_4$H$_9$ | CCl |
| CF$_3$ | Cl | —C(CH$_3$)$_2$O-sec-C$_4$H$_9$ | CNO$_2$ |
| CF$_3$ | Cl | —C(CH$_3$)$_2$O-sec-C$_4$H$_9$ | CF |
| CF$_3$ | Cl | —C(CH$_3$)$_2$O-sec-C$_4$H$_9$ | N |
| CF$_3$ | NO$_2$ | —C(CH$_3$)$_2$O-sec-C$_4$H$_9$ | CNO$_2$ |
| CF$_3$ | F | —C(CH$_3$)$_2$O-sec-C$_4$H$_9$ | CF |
| CF$_3$ | —N(pyrrole) | —C(CH$_3$)$_2$O-sec-C$_4$H$_9$ | CCl |
| OCF$_3$ | Cl | —C(CH$_3$)$_2$O-sec-C$_4$H$_9$ | CCl |
| CF$_3$ | Cl | —C(CH$_3$)$_2$O-isoC$_4$H$_9$ | CCl |
| CF$_3$ | Cl | —C(CH$_3$)$_2$O-isoC$_4$H$_9$ | CNO$_2$ |
| CF$_3$ | Cl | —C(CH$_3$)$_2$O-isoC$_4$H$_9$ | CF |
| CF$_3$ | Cl | —C(CH$_3$)$_2$O-isoC$_4$H$_9$ | N |
| CF$_3$ | NO$_2$ | —C(CH$_3$)$_2$O-isoC$_4$H$_9$ | CNO$_2$ |
| CF$_3$ | F | —C(CH$_3$)$_2$O-isoC$_4$H$_9$ | CF |

TABLE 1-1-continued (R⁴ = H)

| R¹ | R² | R³ | X |
|---|---|---|---|
| CF₃ | —N⟩ (pyrrole) | —C(CH₃)₂O-isoC₄H₉ | CCl |
| OCF₃ | Cl | —C(CH₃)₂O-isoC₄H₉ | CCl |
| CF₃ | Cl | norbornyl | CCl |
| CF₃ | Cl | norbornyl | CNO₂ |
| CF₃ | Cl | norbornyl | CF |
| CF₃ | Cl | norbornyl | N |
| CF₃ | NO₂ | norbornyl | CNO₂ |
| CF₃ | F | norbornyl | CF |
| CF₃ | —N⟩ (pyrrole) | norbornyl | CCl |
| OCF₃ | Cl | norbornyl | CCl |
| CF₃ | Cl | 1-methylcyclohexenyl | CCl |
| CF₃ | Cl | 1-methylcyclohexenyl | CNO₂ |
| CF₃ | Cl | 1-methylcyclohexenyl | CF |
| CF₃ | Cl | 1-methylcyclohexenyl | N |
| CF₃ | NO₂ | 1-methylcyclohexenyl | CNO₂ |
| CF₃ | F | 1-methylcyclohexenyl | CF |
| CF₃ | —N⟩ (pyrrole) | 1-methylcyclohexenyl | CCl |
| OCF₃ | Cl | 1-methylcyclohexenyl | CCl |
| CF₃ | CF₃ | -tert-C₄H₉ | N |
| CF₃ | CF₃ | —C(CH₃)₂SCH₃ | N |
| CF₃ | CF₃ | —CF₂CF₃ | N |
| CF₃ | CF₃ | —CH(CH₃)(CF₃) | N |
| CF₃ | CF₃ | -isoC₃H₇ | N |
| CF₃ | CF₃ | —C(CH₃)=CH₂ | N |
| CF₃ | CF₃ | —CF₂CF₂CF₃ | N |
| CF₃ | CF₃ | —C(CH₃)₂CH₂Cl | N |
| CF₃ | CF₃ | —C(CH₃)₂OCH₃ | N |
| CF₃ | CF₃ | —C(CF₃)₂CH₃ | N |
| CF₃ | CF₃ | —C(CH₃)₂COOC₂H₅ | N |
| CF₃ | CF₃ | -sec-C₄H₉ | N |
| CF₃ | CF₃ | 1-methylcyclopropyl | N |
| CF₃ | CF₃ | 2,2,4,4-tetramethyl-1,3-dithietanyl | N |
| CF₃ | CF₃ | —C(CH₃)₂SO₂CH₃ | N |
| CF₃ | CF₃ | —C(CH₃)₂SC₂H₅ | N |
| CF₃ | CF₃ | —C(CH₃)₂S-n-C₃H₇ | N |
| CF₃ | CF₃ | —C(CH₃)₂SO₂C₂H₅ | N |

TABLE 1-1-continued ($R^4 = H$)

| $R^1$ | $R^2$ | $R^3$ | X |
|---|---|---|---|
| $CF_3$ | $CF_3$ | $-C(CH_3)_2SO_2$-n-$C_3H_7$ | N |
| $CF_3$ | $CF_3$ | $-C_2H_5$ | N |
| $CF_3$ | $CF_3$ | $-C(CH_3)_2C_2H_5$ | N |
| $CF_3$ | $CF_3$ | 1,1-dichloro-2-methylcyclopropyl | N |
| $CF_3$ | $CF_3$ | 1-methylcyclohexyl | N |
| $CF_3$ | $CF_3$ | 1-methylcyclopentyl | N |
| $CF_3$ | $CF_3$ | -n-$C_3H_7$ | N |
| $CF_3$ | $CF_3$ | $-CH(C_2H_5)_2$ | N |
| $CF_3$ | $CF_3$ | $-C(CH_3)_2COOCH_3$ | N |
| $CF_3$ | $CF_3$ | $-C(CH_3)_2$S-iso$C_3H_7$ | N |
| $CF_3$ | $CF_3$ | $-C(CH_3)_2$S-sec-$C_4H_9$ | N |
| $CF_3$ | $CF_3$ | $-C(CH_3)_2$S-iso$C_4H_9$ | N |
| $CF_3$ | $CF_3$ | $-C(CH_3)_2$S-tert-$C_4H_9$ | N |
| $CF_3$ | $CF_3$ | $-C(C_2H_5)_2CH_3$ | N |
| $CF_3$ | $CF_3$ | $-C(CH_3)_2OC_2H_5$ | N |
| $CF_3$ | $CF_3$ | $-C(CH_3)_2$O-n-$C_3H_7$ | N |
| $CF_3$ | $CF_3$ | $-CH_2OCH_3$ | N |
| $CF_3$ | $CF_3$ | $-C(CH_3)_2$O-iso$C_4H_9$ | N |
| $CF_3$ | $CF_3$ | $-C(CH_3)_2$O-sec-$C_4H_9$ | N |
| $CF_3$ | $CF_3$ | norbornyl | N |
| $CF_3$ | $CF_3$ | 4-methylcyclohex-1-enyl | N |
| $CF_3$ | Cl | $C(CH_3)_2S(O)CH_3$ | CCl |
| $CF_3$ | Cl | $C(CH_3)_2S(O)CH_3$ | $CNO_2$ |
| $CF_3$ | Cl | $C(CH_3)_2S(O)CH_3$ | CF |
| $CF_3$ | Cl | $C(CH_3)_2S(O)CH_3$ | N |
| $CF_3$ | $NO_2$ | $C(CH_3)_2S(O)CH_3$ | $CNO_2$ |
| $CF_3$ | F | $C(CH_3)_2S(O)CH_3$ | CF |
| $CF_3$ | pyrrol-1-yl | $C(CH_3)_2S(O)CH_3$ | CCl |
| $OCF_3$ | Cl | $C(CH_3)_2S(O)CH_3$ | CCl |
| $CF_3$ | $CF_3$ | $C(CH_3)_2S(O)CH_3$ | N |

TABLE 1-2

($R^4 = F$)

| $R^1$ | $R^2$ | $R^3$ | X |
|---|---|---|---|
| $CF_3$ | Cl | -tert-$C_4H_9$ | CCl |
| $CF_3$ | Cl | $-C(CH_3)_2SCH_3$ | CCl |
| $CF_3$ | Cl | $-CF_2CF_3$ | CCl |
| $CF_3$ | Cl | $-CH(CH_3)CF_3$ | CCl |
| $CF_3$ | Cl | -iso$C_3H_7$ | CCl |
| $CF_3$ | Cl | $-C(CH_3)=CH_2$ | CCl |
| $CF_3$ | Cl | $-CF_2CF_2CF_3$ | CCl |
| $CF_3$ | Cl | $-C(CH_3)_2CH_2Cl$ | CCl |
| $CF_3$ | Cl | $-C(CH_3)_2OCH_3$ | CCl |
| $CF_3$ | Cl | $-C(CF_3)_2CH_3$ | CCl |
| $CF_3$ | Cl | $-C(CH_3)_2COOC_2H_5$ | CCl |
| $CF_3$ | Cl | -sec-$C_4H_9$ | CCl |
| $CF_3$ | Cl | 1-methylcyclopropyl | CCl |
| $CF_3$ | Cl | 2-methyl-1,3-dithiolan-2-yl | CCl |
| $CF_3$ | Cl | $-C(CH_3)_2SO_2CH_3$ | CCl |
| $CF_3$ | Cl | $-C(CH_3)_2SC_2H_5$ | CCl |
| $CF_3$ | Cl | $-C(CH_3)_2$S-n-$C_3H_7$ | CCl |
| $CF_3$ | Cl | $-C(CH_3)_2SO_2C_2H_5$ | CCl |
| $CF_3$ | Cl | $-C(CH_3)_2SO_2$-n-$C_3H_7$ | CCl |
| $CF_3$ | Cl | $-C_2H_5$ | CCl |
| $CF_3$ | Cl | $-C(CH_3)_2C_2H_5$ | CCl |
| $CF_3$ | Cl | 1,1-dichloro-2-methylcyclopropyl | CCl |
| $CF_3$ | Cl | 1-methylcyclohexyl | CCl |
| $CF_3$ | Cl | 1-methylcyclopentyl | CCl |
| $CF_3$ | Cl | -n-$C_3H_7$ | CCl |
| $CF_3$ | Cl | $-CH(C_2H_5)_2$ | CCl |
| $CF_3$ | Cl | $-C(CH_3)_2COOCH_3$ | CCl |
| $CF_3$ | Cl | $-C(CH_3)_2$S-iso$C_3H_7$ | CCl |
| $CF_3$ | Cl | $-C(CH_3)_2$S-sec-$C_4H_9$ | CCl |
| $CF_3$ | Cl | $-C(CH_3)_2$S-iso$C_4H_9$ | CCl |
| $CF_3$ | Cl | $-C(CH_3)_2$S-tert-$C_4H_9$ | CCl |
| $CF_3$ | Cl | $-C(C_2H_5)_2CH_3$ | CCl |
| $CF_3$ | Cl | $-C(CH_3)_2OC_2H_5$ | CCl |
| $CF_3$ | Cl | $-C(CH_3)_2$O-n-$C_3H_7$ | CCl |

TABLE 1-2-continued (Structure: phenyl ring with R4, R2, R1, X substituents attached via N to oxadiazolone ring with R3; R4 = F)

| R¹ | R² | R³ | X |
|---|---|---|---|
| CF₃ | Cl | —CH₂OCH₃ | CCl |
| CF₃ | Cl | —C(CH₃)₂O-isoC₄H₉ | CCl |
| CF₃ | Cl | —C(CH₃)₂O-sec-C₄H₉ | CCl |
| CF₃ | Cl | (bicycloheptyl) | CCl |
| CF₃ | Cl | (methylcyclohexenyl) | CCl |
| CF₃ | Cl | —C(CH₃)₂S(O)CH₃ | CCl |
| CF₃ | F | -tert-C₄H₉ | CCl |
| CF₃ | F | —C(CH₃)₂SCH₃ | CCl |
| CF₃ | F | —CF₂CF₃ | CCl |
| CF₃ | F | —CH(CH₃)(CF₃) | CCl |
| CF₃ | F | -isoC₃H₇ | CCl |
| CF₃ | F | —C(CH₃)=CH₂ | CCl |
| CF₃ | F | —CF₂CF₂CF₃ | CCl |
| CF₃ | F | —C(CH₃)₂CH₂Cl | CCl |
| CF₃ | F | —C(CH₃)₂OCH₃ | CCl |
| CF₃ | F | —C(CF₃)₂CH₃ | CCl |
| CF₃ | F | —C(CH₃)₂COOC₂H₅ | CCl |
| CF₃ | F | -sec-C₄H₉ | CCl |
| CF₃ | F | (1-methylcyclopropyl) | CCl |
| CF₃ | F | (2-methyl-1,3-dithianyl) | CCl |
| CF₃ | F | —C(CH₃)₂SO₂CH₃ | CCl |
| CF₃ | F | —C(CH₃)₂SC₂H₅ | CCl |
| CF₃ | F | —C(CH₃)₂S-n-C₃H₇ | CCl |
| CF₃ | F | —C(CH₃)₂SO₂C₂H₅ | CCl |
| CF₃ | F | —C(CH₃)₂SO₂-n-C₃H₇ | CCl |
| CF₃ | F | —C₂H₅ | CCl |
| CF₃ | F | —C(CH₃)₂C₂H₅ | CCl |
| CF₃ | F | (2,2-dichloro-1-methylcyclopropyl) | CCl |
| CF₃ | F | (1-methylcyclohexyl) | CCl |
| CF₃ | F | (1-methylcyclopentyl) | CCl |
| CF₃ | F | -n-C₃H₇ | CCl |
| CF₃ | F | —CH(C₂H₅)₂ | CCl |
| CF₃ | F | —C(CH₃)₂COOCH₃ | CCl |
| CF₃ | F | —C(CH₃)₂S-isoC₃H₇ | CCl |
| CF₃ | F | —C(CH₃)₂S-sec-C₄H₉ | CCl |
| CF₃ | F | —C(CH₃)₂S-isoC₄H₉ | CCl |
| CF₃ | F | —C(CH₃)₂S-tert-C₄H₉ | CCl |
| CF₃ | F | —C(C₂H₅)₂CH₃ | CCl |
| CF₃ | F | —C(CH₃)₂OC₂H₅ | CCl |
| CF₃ | F | —C(CH₃)₂O-n-C₃H₇ | CCl |
| CF₃ | F | —CH₂OCH₃ | CCl |
| CF₃ | F | —C(CH₃)₂O-isoC₄H₉ | CCl |
| CF₃ | F | —C(CH₃)₂O-sec-C₄H₉ | CCl |
| CF₃ | F | (bicycloheptyl) | CCl |
| CF₃ | F | (methylcyclohexenyl) | CCl |
| CF₃ | F | —C(CH₃)₂S(O)CH₃ | CCl |
| CF₃ | Cl | -tert-C₄H₉ | CF |
| CF₃ | Cl | —C(CH₃)₂SCH₃ | CF |
| CF₃ | Cl | —CF₂CF₃ | CF |
| CF₃ | Cl | —CH(CH₃)(CF₃) | CF |
| CF₃ | Cl | -isoC₃H₇ | CF |
| CF₃ | Cl | —C(CH₃)=CH₂ | CF |
| CF₃ | Cl | —CF₂CF₂CF₃ | CF |
| CF₃ | Cl | —C(CH₃)₂CH₂Cl | CF |
| CF₃ | Cl | —C(CH₃)₂OCH₃ | CF |
| CF₃ | Cl | —C(CF₃)₂CH₃ | CF |
| CF₃ | Cl | —C(CH₃)₂COOC₂H₅ | CF |
| CF₃ | Cl | -sec-C₄H₉ | CF |
| CF₃ | Cl | (1-methylcyclopropyl) | CF |
| CF₃ | Cl | (2-methyl-1,3-dithianyl) | CF |
| CF₃ | Cl | —C(CH₃)₂SO₂CH₃ | CF |

TABLE 1-2-continued

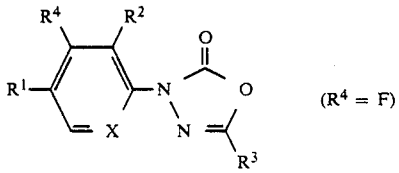

(R⁴ = F)

| R¹ | R² | R³ | X |
|---|---|---|---|
| CF₃ | Cl | —C(CH₃)₂SC₂H₅ | CF |
| CF₃ | Cl | —C(CH₃)₂S-n-C₃H₇ | CF |
| CF₃ | Cl | —C(CH₃)₂SO₂C₂H₅ | CF |
| CF₃ | Cl | —C(CH₃)₂SO₂-n-C₃H₇ | CF |
| CF₃ | Cl | —C₂H₅ | CF |
| CF₃ | Cl | —C(CH₃)₂C₂H₅ | CF |
| CF₃ | Cl | (dichlorocyclopropyl-CH₃) | CF |
| CF₃ | Cl | (methylcyclohexyl) | CF |
| CF₃ | Cl | (methylcyclopentyl) | CF |
| CF₃ | Cl | -n-C₃H₇ | CF |
| CF₃ | Cl | —CH(C₂H₅)(C₂H₅) | CF |
| CF₃ | Cl | —C(CH₃)₂COOCH₃ | CF |
| CF₃ | Cl | —C(CH₃)₂S-isoC₃H₇ | CF |
| CF₃ | Cl | —C(CH₃)₂S-sec-C₄H₉ | CF |
| CF₃ | Cl | —C(CH₃)₂S-isoC₄H₉ | CF |
| CF₃ | Cl | —C(CH₃)₂S-tert-C₄H₉ | CF |
| CF₃ | Cl | —C(C₂H₅)₂CH₃ | CF |
| CF₃ | Cl | —C(CH₃)₂OC₂H₅ | CF |
| CF₃ | Cl | —C(CH₃)₂O-n-C₃H₇ | CF |
| CF₃ | Cl | —CH₂OCH₃ | CF |
| CF₃ | Cl | —C(CH₃)₂O-isoC₄H₉ | CF |
| CF₃ | Cl | —C(CH₃)₂O-sec-C₄H₉ | CF |
| CF₃ | Cl | (bicyclic group) | CF |
| CF₃ | Cl | (methylcyclohexenyl) | CF |
| CF₃ | Cl | C(CH₃)₂S(O)CH₃ | CF |

Examples of harmful insects against which the compounds of the present invention exhibit remarkable effects include the following:

Harmful Insects Belonging to Hemiptera

Planthoppers such as small brown planthopper (*Laodelphax striatellus*), brown planthopper (*Nilaparvata lugens*), white-backed rice planthopper (*Sogatella furcifera*), etc.; leafhoppers such as green rice leafhopper (*Nephotettix cinticeps*), (*Nephotettix virescens*), etc.; aphids, bugs, whiteflies, scales, lace bugs, psyllids, etc.

Lepidoptera

Pyralid moths such as rice stem borer (*Chilo suppressalis*), rice leafroller (*Cnaphalocrocis medinalis*), Indian meal moth (*Plodia interpunctella*), etc.; moths such as tobacco cutworm (*Spodoptera litura*), rice armyworm (*Pseudaletia separata*), cabbage armyworm (*Mamestra brassicae*), etc.; Pieridae such as common cabbageworm (*Pieris rapae crucivora*), etc.; Tortricidae or tortricid moths such as Adoxophyes spp., Grapholita spp., etc.; Carposinidae, lyonetiid moths (Lyonetiidae), tussock moths (*Lymantriidae*), beet semi-looper (*Autographa nigrisigna*); harmful insects belonging to Agrothis spp. such as turnip cutworm (*Agrothis segetum*), black cutworm (*Agrothis ipsilon*); harmful insects belonging to Hiliothis spp.; diamondback moth (*Plutella xylostella*), clothes moths (Tineidae), casemaking clothes moth (*Tinea translucens*), webbing clothes moth (*Tineola bisselliella*); etc.

Harmful Insects Belonging to Diptera

Mosquitos such as common mosquito (*Culex pipiens pallens*), *Culex tritaeniorhynchus*, etc.; Aedes spp. such as *Aedes aegypti*, *Aedes albopictus*, etc.; midges (Chironomidae); Muscidae such as housefly (*Musca domestica*), false stablefly (*Muscina stabulans*), etc. Calliphoridae; Sarcophagidae; lesser housefly (*Fannia canicularis*); Anthomyiidae or anthomyiid flies such as seedcorn maggot (*Delia platura*), onion maggot (*Delia antiqua*), etc.; fruit flies (Tephritidae); small fruit flies (Drosophilidae); moth flies (Psychodidae); black flies (Simuliidae); Tabanidae; stable flies (Stomoxyidae); etc. Harmful insects belonging to Coleoptera:

Corn root worms such as western corn rootworm (*Diabrotica virgifera*), southern corn root worm (*Diabrotica undecimpunctata*), etc.; scarabs (Scarabaeidae) such as cupreous chafer (*Anomala cuprea*), soybeen beetle (*Anomala rufocuprea*), etc.; weevils such as maize weevil (*Sitophilus zeamais*), rice water weevil (*Lissorhoptrus oryzophilus*), adzuki been weevil (*Callosobruchys chineneis*), etc.; darkling beetles (Tenebrionidae) such as yellow mealworm (*Tenebrio molitor*), red fluor beetle (*Tribolium castaneum*), etc.; leaf beetles (Chrysomelidae) such as cucrubit leaf beetle (*Aulacophora femoralis*), striped flea beetles (*Phyllotreta striolata*), etc.; Anobiidae; Epilachna spp. such as twenty-eight-spotted ladybirds (*Epilachna vigintioctopunctata*), etc.; powderpost beetles (Lyctidae); false powderpost beetles (Bostrychidae), Cerambycidae; robe beetle (*Paederus fusipes*), etc.

Harmful Insects Belonging to Dictyoptera

German cockroach (*Blattella germanica*), smoky-brown cockroach (*Periplaneta fuliginosa*), American cockroach (*Periplaneta americana*), brown cockroach (*Periplaneta brunnea*), oriental cockroach (*Blatta orientalis*), Japanese cockroach (*Periplaneta japonica*), etc.

Harmful Insects Belonging to Thysanoptera

Thrips palmi, flower thrips (*Thrips hawaiiensis*), etc.

Harmful Insects Belonging to Hymenoptera ants (Formicidae); hornets (Vespidae); bethylid wasps (Bethylidae); sawflies (Tenthredinidae) such as cabbage sawfly (Athalia rosae ruficornis), etc.

Harmful Insects Belonging to Orthoptera mole crickets (Gryllotalpidae); grasshoppers (Acrididae), etc.;

Harmful Insects Belonging to Aphaniptera

*Purex irritans*, etc.

Harmful Insects Belonging to Anoplura

*Pediculus humanus capitis, Pythirus pubis*, etc.

Harmful Insects Belonging to Isoptera

*Reticulitermes speratus*, Formosan subterranean termite (*Coptotermes formosanus*), etc.

Moreover, the compounds of the present invention are very effective to the insects which develop the resistance against conventional insecticides.

In the case that the compounds of the present invention are used as the active ingredient of insecticidal compositions, the compounds may be used as they are, without adding any other components but in general, the compounds are mixed with a solid carrier, a liquid carrier, a gaseous carrier, a feed, etc. and, if necessary and desired, the mixture is further supplemented with a surfactant and other adjuvants used to prepare insecticidal preparations and prepared into forms such as oil sprays, emulsifiable concentrates, wettable powders, flowable concentrates, granules, dusts, aerosol, fumigants (fogging, etc.), poison bait, etc.

These formulations contain generally 0.01 to 95% by weight of the compounds of the present invention as the active ingredient.

Examples of the solid carrier used for making formulations include fine powders or granulates, etc. of clays (kaolin clay, diatomaceous earth, synthetic hydrated silicon dioxide, bentonite, Fubasami clay terra alba, etc.), talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.), etc. Examples of the liquid carrier include water, alcohols (methanol, ethanol, etc.), ketones (acetone, methyl ethyl ketone, etc.), aromatic hydrocarbons (benzene, toluene, xylene, ethylbenzene, methylnaphthalene, etc.), aliphatic hydrocarbons (hexane, cyclohexane, kerosene, gas oil, etc.), esters (ethyl acetate, butyl acetate, etc.), nitriles (acetonitrile, isobutyronitrile, etc.), ethers (diisopropyl ether, dioxan, etc.), acid amides (N,N-dimethylformamide, N,N-dimethylacetamide, etc.), halogenated hydrocarbons (dichloromethane, trichloroethane, carbon tetrachloride, etc.), dimethylsulfoxide; vegetable oils such as soybean oil, cotton seed oil, etc. Examples of the gaseous carrier, i.e., propellant, include freon gas, butane gas, LPG (liquefied petroleum gas), dimethyl ether, carbon dioxide, etc.

Examples of the surfactant include alkyl sulfates, alkyl sulfonates, alkylaryl sulfonates, alkyl aryl ethers and polyoxyethylene derivatives thereof, polyethylene glycol ether, polyvalent alcohol esters, sugar alcohol derivatives, etc.

Examples of the adjuvants such as binders, dispersing agents, etc. for formulations include casein, gelatin, polysaccharides (starch powders, gum arabic, cellulose derivatives, alginic acid, etc.), lignin derivatives, bentonite, sugars, synthetic water-soluble high molecular substances (polyvinyl alcohol, polyvinyl-pyrrolidone, polyacrylic acid, etc.). Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, and the like.

As a base material for the poison baits, there are, for example, feed components such as crop powders, essential vegetable oil, sugars, crystalline cellulose etc.; antioxidants such as dibutylhydroxytoluene, nordihydroguaiaretic acid, etc.; preservatives such as dehydroacetic acid, etc.; feeding error preventing agents such as red peper powders, etc.; incentive flavor such as cheese flavor, onion flavor, etc.

The thus obtained formulations may be used as they are or after diluting with water, etc. Alternatively, the formulations may be used as admixture with other insecticides, nematocides, acaricides, bacteriocides, herbicides, plant growth regulators, synergistic agents, fertilizers, soil conditioners, animal feed, etc., or may also be used simultaneously with them, without mixing therewith.

Where the compounds of the present invention are used as insecticides for agricultural use, the dose is generally 0.1 g to 100 g per 10 ares; when emulsifiable concentrates, wettable powders, flowable concentrates, etc. are used after diluting them with water, the concentration is 1 ppm to 500 ppm. Granules, dusts, etc. may be used as they are, without diluting them. For purposes of household and public hygiene, emulsifiable concentrates, wettable powders, flowable concentrates, etc. are diluted with water in a concentration of 1 ppm to 500 ppm; oils, aerosol, fumigants, poison baits, etc. may be used as they are.

These doses and concentrations may vary depending upon kind of formulations, timing for application, place applied, method for application, kinds of insect, condition of damages, etc. and may be increased or decreased, irrespective of the ranges set forth above.

Hereafter the present invention is described in more detail, by referring to production examples, formulation examples and test examples but is not deemed to these examples.

PRODUCTION EXAMPLE 1

(Production of Compound No. (1))

In 4.6 ml (8.9 mmols) of 20% phosgene-toluene solution, 0.33 g (1 mmol) of N'-(2,6-dichloro-4-trifluoromethylphenyl)-2,2-dimethylpropionhydrazide was heated to reflux for 16 hours (inner temperature of 80° C.). Then, an excess of phosgene and toluene was distilled off. After the residue was dissolved in 5 ml of methylene chloride, 0.65 g (6.4 mmols) of triethylamine was added to the solution and the mixture was heated to reflux for 30 minutes. Next, the mixture was washed with water, dried over anhydrous sodium sulfate and then concentrated under reduced pressure. The thus obtained crude product was subjected to silica gel column chromatography to give 0.16 g of 5-(1,1-dimethylethyl)-3-(2,6-dichloro-4-trifluoromethylphenyl)-1,3,4-oxadiazolin-2-one.

m.p. 143.0° C.

PRODUCTION EXAMPLE 2

(Production of Compound No. (2))

To a mixture of 0.35 g (1 mmol) of N'-(2,6-dichloro-4-trifluoromethylphenyl)-2-methyl-2-methylthiopropionhydrazide, 0.25 g (2.5 mmols) of triethylamine and 5 ml of dioxan was dropwise added 0.24 g (1.2 mmol) of trichloromethyl chloroformate. After completion of the dropwise addition, the mixture was heated to reflux for 3 hours. The mixture was concentrated under reduced pressure and the residue was taken up in ether. After washing with water and saturated sodium bicarbonate aqueous solution, the solution was dried over anhydrous sodium sulfate and then concentrated under reduced pressure. The thus obtained crude product was subjected to silica gel column chromatography to give 0.17 g of 5-(1-methyl-1-methylthioethyl)-3-(2,6-dichloro-4-trifluoromethylphenyl)-1,3,4-oxadiazolin-2-one.

m.p. 92.0° C.

PRODUCTION EXAMPLE 3

(Production of Compound No. (3))

After 44 mg (1.1 mmol) of 60% sodium hydride was added to a solution of 0.14 g (1 mmol) of 5-(1-methylcyclopropyl)-1,3,4-oxadiazolin-2-one in 5 ml of N,N-dimethylformamide at room temperature, the mixture was stirred at the same temperature for 15 minutes. To the mixture was added 0.25 g (1 mmol) of 3,4,5-trichlorobenzotrifluoride followed by heating a 80° C. for 6 hours. After cooling, the mixture was poured into water and extracted with ethyl acetate. After drying over magnesium sulfate, the extract was concentrated under reduced pressure to give the crude product. The crude product was subjected to silica gel column chromatography to give 35 mg of 5-(1-methylcyclopropyl)-3-(2,6-dichloro-4-trifluoromethylphenyl)-1,3,4-oxadiazoline-2-one.

m.p. 107.1° C.

PRODUCTION EXAMPLE 4

(Production of Compound No. (4))

A mixture of 0.35 g (1 mmol) of N'-(2,6-dinitro-4-trifluoromethylphenyl)-2,2-dimethylpropionhydrazide, 0.3 g (3.1 mmols) of phosgene and 2.1 ml of toluene was heated to reflux for 2.5 hours (inner temperature of 59° C.). A solution (0.7 ml) of 0.1 g (1 mmol) of phosgene in toluene was further added to the reaction mixture followed by heating to reflux for further 2.5 hours. An excess of phosgene and toluene were distilled off and the residue was taken up in 20 ml of ether. After washing with saturated sodium chloride aqueous solution, the solution was dried over anhydrous sodium sulfate and then concentrated under reduced pressure. The thus obtained crude product was subjected to silica gel column chromatography to give 0.17 g of 5-(1,1-dimethylethyl)-3-(2,6-dinitro-4-trifluoromethylphenyl)-1,3,4-oxadiazolin-2-one.

m.p. 146.0° C.

Compounds produced according to Production Examples are shown in Table 2.

TABLE 2

(R⁴ = H)

| Compound No. | $R^1$ | $R^2$ | $R^3$ | X | Physical constant |
|---|---|---|---|---|---|
| (1) | $CF_3$ | Cl | -tert-$C_4H_9$ | CCl | m.p. 143.0° C. |
| (2) | $CF_3$ | Cl | $-C(CH_3)_2SCH_3$ | CCl | m.p. 92.0° C. |
| (3) | $CF_3$ | Cl | cyclopropyl-$CH_3$ | CCl | m.p. 107.1° C. |
| (4) | $CF_3$ | $NO_2$ | -tert-$C_4H_9$ | $CNO_2$ | m.p. 146.0° C. |
| (5) | $CF_3$ | Cl | $-C(CH_3)_2SO_2CH_3$ | CCl | m.p. 153.2° C. |
| (6) | $CF_3$ | Cl | $-C(CH_3)_2SC_2H_5$ | CCl | $n_D^{24.0}$ 1.5152 |
| (7) | $CF_3$ | Cl | $-C(CH_3)_2S$-n-$C_3H_7$ | CCl | $n_D^{24.0}$ 1.5159 |
| (8) | $CF_3$ | Cl | $-C(CH_3)_2C_2H_5$ | CCl | m.p. 67.2° C. |
| (9) | $CF_3$ | Cl | $-CF_2CF_3$ | CCl | $n_D^{24.0}$ 1.4421 |
| (10) | $CF_3$ | $NO_2$ | $-C(CH_3)_2SCH_3$ | $CNO_2$ | m.p. 121.7° C. |
| (11) | $CF_3$ | $NO_2$ | cyclopropyl-Cl,Cl,$CH_3$ | $CNO_2$ | m.p. 144.2° C. |
| (12) | $CF_3$ | Cl | -tert-$C_4H_9$ | CF | m.p. 94.4° C. |
| (13) | $CF_3$ | Cl | $-C(CH_3)_2SCH_3$ | CF | $n_D^{22.5}$ 1.4919 |
| (14) | $CF_3$ | Cl | cyclopropyl-$CH_3$ | CF | m.p. 81.7° C. |
| (15) | $CF_3$ | Cl | cyclohexyl-$CH_3$ | CF | $n_D^{25.2}$ 1.4879 |
| (16) | $CF_3$ | Cl | -tert-$C_4H_9$ | N | $n_D^{25.2}$ 1.4842 |

TABLE 2-continued

[Structure: R¹, R², R⁴, X on a benzene ring attached to N-N with a carbonyl-O-C(R³) ring; (R⁴ = H)]

| Compound No. | R¹ | R² | R³ | X | Physical constant |
|---|---|---|---|---|---|
| (17) | $CF_3$ | Cl | $-C(CH_3)_2SCH_3$ | N | $n_D^{25.2}$ 1.5152 |
| (18) | $CF_3$ | Cl | [norbornyl group] | CCl | m.p. 118.1° C. |
| (19) | $CF_3$ | Cl | -tert-$C_4H_9$ | $CNO_2$ | m.p. 109.7° C. |
| (20) | $CF_3$ | Cl | $-C(CH_3)_2OC_2H_5$ | CCl | m.p. 62.7° C. |
| (21) | $CF_3$ | Cl | $-C(CH_3)_2OCH_3$ | CCl | $n_D^{24.2}$ 1.4949 |
| (22) | $CF_3$ | Cl | $-C(CH_3)_2SCH_3$ | $CNO_2$ | m.p. 100.5° C. |
| (23) | $C_3F_7$ | Cl | $-C(CH_3)_2SCH_3$ | CCl | $n_D^{22.6}$ 1.4853 |
| (24) | $CF_3$ | Cl | $-C(CH_3)_2SOCH_3$ | CCl | $n_D^{25.2}$ 1.5141 |
| (25) | $CF_3$ | F | $-C(CH_3)_2SCH_3$ | CF | $n_D^{24.2}$ 1.4874 |
| (26) | $CF_3$ | Cl | $-C(CH_3)_2O\text{-iso}C_3H_7$ | CCl | $n_D^{24.3}$ 1.4869 |
| (27) | $CF_3$ | Cl | $-C(=CH_2)CH_3$ | CCl | m.p. 93.2° C. |
| (28) | $CF_3$ | Cl | $-CF_2CF_3$ | CF | $n_D^{23.8}$ 1.4269 |
| (29) | $CF_3$ | $CF_3$ | $-C(CH_3)_2SCH_3$ | N | $n_D^{22.7}$ 1.4781 |
| (30) | $CF_3$ | Cl | [methylcyclohexenyl group with $CH_3$] | CCl | $n_D^{26.0}$ 1.5092 |

Next, Formulation examples are shown, wherein parts are all by weight and the compounds of the present invention are designated by the compound numbers shown in Table 2.

FORMULATION EXAMPLE 1

Emulsifiable Concentrate

After 10 parts each of Compounds (1) through (30) of the present invention are dissolved in 35 parts of xylene and 35 parts of dimethylformamide, 14 parts of polyoxyethylene styrylphenyl ether and 6 parts of calcium dodecylbenzenesulfonate are added to the solutions. The resulting mixtures are thoroughly mixed stirred to give 10% emulsifiable concentrate, respectively.

FORMULATION EXAMPLE 2

Wettable Powder

After 20 parts of Compound (2) of the present invention are added to a mixture of 4 parts of sodium laurylsulfate, 2 parts of calcium ligninsulfonate, 20 parts of synthetic hydrated silicon dioxide fine powders and 54 parts of diatomaceous earth, the mixture is mixed and stirred with a juice mixer to give 20% wettable powder.

FORMULATION EXAMPLE 3

Granule (In the Case of Solid Active Ingredient)

After 5 parts of synthetic hydrated silicon dioxide fine powders, 5 parts of sodium dodecylbenzenesulfonate, 30 parts of bentonite and 55 parts of clay are added to 5 parts of Compound (5) of the present invention, the mixture is thoroughly mixed and stirred. A suitable amount of water is further added to the mixture followed by stirring. The mixture is granulated with a granulator and air-dried to give 5% granule.

FORMULATION EXAMPLE 4

Dust

After 1 part of Compound (13) of the present invention is dissolved in a appropriate amount of acetone, 5 parts of synthetic hydrated silicon dioxide fine powders, 0.3 part of PAP and 93.7 parts of clay are added to the solution. The mixture is mixed and stirred with a juice mixer and acetone is evaporated off to give 1% dust.

FORMULATION EXAMPLE 5

Flowable Concentrate (In the Case of Solid Active Ingredient)

After 20 parts of Compound (3) of the present invention and 1.5 part of sorbitan trioleate are mixed with 28.5 parts of an aqueous solution containing 2 parts of polyvinyl alcohol, the mixture is finely divided (less than 3μ in particle diameter) with a sand grinder. Then, 40 parts of aqueous solution containing 0.05 part of xanthane gum and 0.1 part of aluminum magnesium silicate are added to the powders and 10 parts of propylene glycol are further added thereto. The mixture is thoroughly mixed and stirred to give 20% flowable concentrate for aqueous suspension.

FORMULATION EXAMPLE 6

Oil Spray

After 0.1 part of Compound (2) of the present invention is dissolved in 5 parts of xylene and 5 parts of trichloroethane, the solution is mixed with 89.9 parts of deodorized kerosene to give 0.1% oil spray.

FORMULATION EXAMPLE 7

Oil-Based Aerosol

After 0.1 part of Compound (2) of the present invention, 0.2 part of tetramethrin, 0.1 part of d-phenothrin, 10 parts of trichloroethane and 59.6 parts of deodorized kerosene are mixed with each other and dissolved. The solution is filled in an aerosol container. After a valve is mounted to the container, 30 parts of propellant (liquefied petroleum gas) are filled under pressure through the valve to give oil-based aerosol.

FORMULATION EXAMPLE 8

Water-Based Aerosol

After 0.2 part of Compound (2) of the present invention, 0.2 part of d-allethrin, 0.2 part of d-phenothrin, 5 parts of xylene, 3.4 parts of deodorized kerosene and 1 part of emulsifier [ATMOS 300 (registered trademark, Atlas Chemical Co., Ltd.)] are mixed with each other and dissolved. The solution and 50 parts of distilled water are filled in an aerosol container. After a valve is mounted to the container, 40 parts of propellant (liquefied petroleum gas) are filled under pressure through the valve to give water-based aerosol.

FORMULATION EXAMPLE 9

Mosquito Coil

After 0.3 g of d-allethrin is added to 0.3 g of Compound (2) of the present invention, the mixture is dissolved in 20 ml of acetone. The solution is then uniformly mixed with 99.4 g of carrier for mosquito-coil (taba powder : sake lees powder wood powder of 4:3:3) with stirring and 120 ml of water is then added to the mixture. The mixture is thoroughly kneaded, molded and dried to give mosquito-coil.

FORMULATION EXAMPLE 10

Electric Mosquito Mat

Acetone is added to 0.4 g of Compound (2) of the present invention, 0.4 g of d-allethrin and 0.4 g of piperonyl butoxide to dissolve and make the whole volume 10 ml. This solution, 0.5 ml, is uniformly impregnated with a base material for electric mat (a mixture of cotton linter and pulp solidified in a plate-like form) having 2.5 cm × 1.5 cm and a thickness of 0.3 cm to give an electric mosquito mat.

FORMULATION EXAMPLE 11

Fumigant

After 100 mg of Compound (13) of the present invention is dissolved in a appropriate amount of acetone, the solution is impregnated with a porous ceramic plate having 4.0 cm × 4.0 cm and a thickness of 1.2 cm to give a fumigant.

FORMULATION EXAMPLE 12

Poison Bait

After 10 mg of Compound (13) of the present invention is dissolved in a 0.5 ml acetone, the solution is applied to 5 g of the powder of dry animal food. The powder is dried to give a 0.5% poison bait.

Next, effectiveness of the compounds of the present invention as the active ingredient of insecticidal compositions is described below, with reference to test examples, wherein the compounds of the present invention are designated by the compound numbers shown in Table 2 and compounds used for comparison and control are designated by the compound numbers shown in Table 3.

TABLE 3

| Compound Symbol | Chemical Structure | Note |
|---|---|---|
| (A) | [structure: 2,4-dichlorophenyl group attached to N-N with acetyl-O and tert-$C_4H_9$ substituents] | Compound described in U.S. Pat. No. 3,385,862 |

TEST EXAMPLE 1

(Insecticidal Test on Nymphs of Brown Planthopper)

The emulsifiable concentrate of the test compound prepared according to Formulation Example 1 was diluted with water (corresponding to 500 ppm) and a rice plant seedling (length of about 12 cm) was immersed in the dilution for a munute. After air-drying, the rice plant seedling was put in a test tube and about 30 nymphs of brown planthopper (*Nilaparvata lugens*) were released. Six days after, the nymphs were observed if they were alive or dead. Criterion for the judgement is as follows.

a: no insect was alive.
b: alive insects were 5 or less.
c: alive insects were 6 or more.

The results are shown in Table 4.

TABLE 4

| Test Compound | Efficacy |
|---|---|
| (1) | a |
| (2) | a |
| (3) | a |
| (5) | a |
| (10) | a |
| (12) | a |
| (13) | a |
| (14) | a |
| (15) | a |
| (16) | a |
| (17) | a |
| (18) | a |
| (19) | a |
| (20) | a |
| (21) | a |
| (22) | a |
| (23) | a |
| (24) | a |
| (25) | a |
| (26) | a |
| (27) | a |
| (29) | a |
| (30) | a |
| (A) | c |
| Untreated | c |

TEST EXAMPLE 2

(Insecticidal Test on Southern Corn Rootworm)

On the bottom of a polyethylene cup having a diameter of 5.5 cm, a filter paper which is of the same size was laid down and 1 ml of an aqueous dilution (500 or 50 ppm) of the emulsifiable concentrate of the test compound prepared according to Formulation Example 1 was dropped onto the filter paper and one corn sprout was put as feed. About 30 eggs of southern corn rootworm (*Diabrotica undecimpunctata*) were put in the cup. Eight days after the cup was covered, dead or alive larvae hatched were examined. Criterion for the judgement is as follows.

a: no insect was alive.
b: alive insects were 5 or less.
c: alive insects were 6 or more.

The results are shown in Table 5.

TABLE 5

| Test Compound | Efficacy | |
|---|---|---|
| | 500 ppm | 50 ppm |
| (1) | a | a |
| (2) | a | a |
| (3) | a | a |
| (5) | a | a |
| (12) | a | a |
| (13) | a | a |
| (14) | a | a |
| (16) | a | a |
| (18) | a | a |
| (19) | a | a |
| (21) | a | a |
| (22) | a | a |
| (24) | a | a |
| (25) | a | a |
| (26) | a | a |
| (27) | a | a |
| (29) | a | a |
| Untreated | c | c |

TEST EXAMPLE 3

(Insecticidal Test on Common Mosquito)

The emulsifiable concentrate of the test compound prepared according to Formulation Example 1 was diluted with water and 0.7 ml of the dilution was added to 100 ml of ion exchange water (concentration of the effective ingredient was 3.5 ppm). In the mixture were released 20 last instar larvae of common mosquito (*Culex pipiens pallens*). One day after the release, mortality was examined.

Criterion for the judgement is as follows.
a: 90% or more
b: not less than 10% but less than 90%
c: less than 10%

The results are shown in Table 6.

TABLE 6

| Test Compound | Mortality (%) |
|---|---|
| (1) | a |
| (2) | a |
| (3) | a |
| (5) | a |
| (12) | a |
| (13) | a |
| (14) | a |
| (20) | a |
| (21) | a |
| (22) | a |
| (23) | a |
| (24) | a |
| (25) | a |
| (29) | a |
| (30) | a |
| (A) | c |
| Untreated | c |

TEST EXAMPLE 4

(Insecticidal Test on German Cockroach)

On the bottom of a polyethylene cup having a diameter of 5.5 cm, a filter paper which is of the same size was laid down and 0.7 ml of an aqueous dilution (500 ppm) of the emulsifiable concentrate of the test compound prepared according to Formulation Example 1 was dropped onto the filter paper. As feed, 30 mg of sucrose was uniformly spread thereon. In the cup, 10 adult males of German cockroach (*Blattella germanica*) were released. Six days after the cup was covered, dead or alive insects were examined to determine mortality.

The results are shown in Table 7.

TABLE 7

| Test Compound | Mortality (%) |
|---|---|
| (1) | 100 |
| (2) | 100 |
| (5) | 100 |
| (10) | 100 |
| (12) | 100 |
| (13) | 100 |
| (14) | 100 |
| (16) | 100 |
| (17) | 100 |
| (19) | 100 |
| (21) | 100 |
| (22) | 100 |
| (23) | 100 |
| (24) | 100 |
| (25) | 100 |
| (26) | 100 |
| (29) | 100 |
| (A) | 0 |
| Untreated | 0 |

TEST EXAMPLE 5

(Insecticidal Test on Housefly)

On the bottom of a polyethylene cup having a diameter of 5.5 cm, a filter paper which is of the same size was laid down and 0.7 ml of an aqueous dilution (500 ppm) of the emulsifiable concentrate of the test compound prepared according to Formulation Example 1 was dropped onto the filter paper. As feed, 30 mg of sucrose was uniformly spread thereon. In the cup, 10 adult females of housefly (*Musca domestica*) were released. Fourty eight hours after the cup was covered, dead or alive insects were examined to determine mortality (2 replications). The results are shown in Table 8.

TABLE 8

| Test Compound | Mortality (%) |
|---|---|
| (2) | 100 |
| (13) | 100 |
| (24) | 100 |
| (A) | 100 |
| Untreated | 0 |

What is claimed is:

1. An oxadiazolinone derivative represented by the general formula:

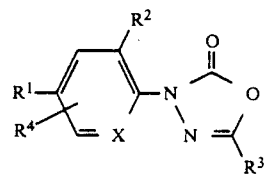

wherein $R^1$ is a $C_1$–$C_3$ haloalkyl group or a $C_1$–$C_3$ haloalkoxy group; $R^2$ is a halogen atom, nitro group, trifluoromethyl group or 1-pyrrolyl group; $R^3$ is a $C_7$ bicycloalkyl group, a methyl- or chloro-substituted $C_3$–$C_6$ cycloalkyl group, a $C_2$–$C_5$ alkenyl group, a methyl-substituted $C_5$–$C_6$ cycloalkenyl group, 2-methyl-1,3-dithioran-2-yl group or a $C_1$–$C_5$ alkyl group, wherein the alkyl group may be substituted with a halogen atom, a $C_1$–$C_3$ alkoxy group, a $C_1$–$C_3$ alkylthio group, a $C_1$–$C_3$ alkylsulfinyl group, a $C_1$–$C_3$ alkylsulfonyl group or a $C_1$–$C_3$ alkoxycarbonyl group; $R^4$ is hydrogen atom; and X is $CR^2$ or N.

2. An oxadiazolinone derivative according to claim 1, wherein $R^1$ is a $C_1$–$C_3$ haloalkyl group; $R^2$ is a halogen atom or nitro group; $R^3$ is a $C_1$–$C_5$ alkyl group, which alkyl group may be substituted with a halogen atom, a $C_1$–$C_3$ alkoxy group, a $C_1$–$C_3$ alkylthio group, a $C_1$–$C_3$ alkylsulfinyl group or a $C_1$–$C_3$ alkylsulfonyl group; and X is $CR^2$.

3. An oxadiazolinone derivative according to claim 2, wherein $R^1$ is trifluoromethyl group; and $R^3$ is a $C_1$–$C_5$ alkyl group, which alkyl group may be substituted with an alkoxy group, a $C_1$–$C_3$ alkylthio group, a $C_1$–$C_3$ alkylsulfinyl group or a $C_1$–$C_3$ alkylsulfonyl group.

4. An oxadiazolinone derivative according to claim 3, wherein $R^3$ is a $C_1$–$C_5$ alkyl group, which alkyl group may be substituted with a $C_1$–$C_5$ alkylthio group or a $C_1$–$C_3$ alkylsulfonyl group.

5. An oxadiazolinone derivative according to claim 4, which is 5-(1-methylthio-1-methylethyl)-3-(2-chloro-6-fluoro-4-trifluoromethylphenyl)-1,3,4-oxadiazolin-2-one.

6. An oxadiazolinone derivative according to claim 4, which is 5-(1,1-dimethylethyl)-3-(6-chloro-2-nitro-4-trifluoromethylphenyl)-1,3,4-oxadiazolin-2-one.

7. An oxadiazolinone derivative according to claim 4, which is 5-(1-methylthio-1-methylethyl)-3-(2,6-dichloro-4-trifluoromethylphenyl)-1,3,4-oxadiazolin-2-one.

8. An oxadiazolinone derivative according to claim 4, which is 5-(1-methylsulfonyl-1-methylethyl)-3-(2,6-dichloro-4-trifluoromethylphenyl)-1,3,4-oxadiazolin-2-one.

9. An insecticidal composition which comprises an insecticidally effective amount of the oxadiazolinone derivative according to claim 1 and an inert carrier.

10. A method for controlling insect pests which comprises applying an insecticidally effective amount of the oxadiazolinone derivative according to claim 1 to the insect pests.

* * * * *